United States Patent [19]

Mitchell et al.

[11] Patent Number: 4,761,507
[45] Date of Patent: Aug. 2, 1988

[54] ISOMERIZATION OF LINALYL HALIDES WITH QUATERNARY SALTS

[75] Inventors: Peter W. D. Mitchell, Freehold, N.J.; Lois T. McElligott, Abington, Pa.; David E. Sasser, Jacksonville, Fla.

[73] Assignee: Union Camp Corporation, Wayne, N.J.

[21] Appl. No.: 750,691

[22] Filed: Jun. 28, 1985

Related U.S. Application Data

[63] Continuation-in-part of Ser. No. 515,564, Jul. 20, 1983, abandoned.

[51] Int. Cl.$^4$ .............................................. C07C 21/19
[52] U.S. Cl. ................................................... 570/236
[58] Field of Search ........................................ 570/236

[56] References Cited

U.S. PATENT DOCUMENTS

| | | | |
|---|---|---|---|
| 2,104,789 | 1/1938 | Carothers | 570/236 |
| 2,123,504 | 7/1938 | Dykstra | 570/236 |
| 2,871,271 | 1/1959 | Booth | 570/231 |
| 3,819,730 | 6/1974 | Nakata et al. | 570/236 |
| 3,836,592 | 6/1974 | Gordon | 570/236 |
| 3,927,130 | 12/1975 | Kadowaki et al. | 570/236 |

FOREIGN PATENT DOCUMENTS

160206 12/1975 Japan ................................... 570/236

*Primary Examiner*—Howard T. Mars
*Attorney, Agent, or Firm*—Kane, Dalsimer, Sullivan, Kurucz, Levy, Eisele & Richard

[57] ABSTRACT

A method for the isomerization of linalyl halides is disclosed, improved by the presence of an organic quaternary salt. The improved method of the invention requires less energy for completion of the isomerization and shortens the isomerization times.

8 Claims, No Drawings

ISOMERIZATION OF LINALYL HALIDES WITH QUATERNARY SALTS

CROSS-REFERENCE TO RELATED APPLICATION

This application is a continuation-in-part of copending U.S. application Ser. No. 515,564 filed July 20, 1983, now abandoned.

BACKGROUND OF THE INVENTION

1. Field of the Invention

The invention relates to the isomerization of linalyl halides.

2. Brief Description of the Prior Art

It is known in the prior art to isomerize simple allylic halides, notably the dichlorobutenes, to their allylic isomers in the presence of a copper catalyst in combination with an organic quaternary salt (U.S. Pat. Nos. 3,819,730 to Nakata and 3,836,592 to Gordon). In spite of the availability of these known methods of isomerization, there has remained a need for economical processes, saving of energy and operating at lower temperatures, for isomerizing more complex allylic halides, notably linalyl chloride. The shortcomings of the prior art methods are evident when they are applied to the halides obtained by hydrohalogenation of myrcene, principally the linalyl halides. In particular, the use of elevated temperatures which leads to low yields because of extensive rearrangement of linalyl to terpinyl halides, an undesirable side reaction unique to the myrcene hydrohalides.

The method of the present invention is such an improvement over the prior art, requiring low temperatures and short isomerization times.

SUMMARY OF THE INVENTION

The invention comprises a novel method for isomerizing linalyl halide to neryl and geranyl halides comprising isomerizing the linalyl halide in the presence of a catalytic proportion of a copper-containing catalyst, and further comprising carrying out the isomerization at a temperature below 25° C. in the presence of a catalytic proportion of an anhydrous hydrogen halide and an organic quaternary salt which has a carbon atom content of at least twenty. The quaternary salt is selected from those of the formula:

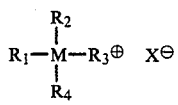

wherein X is selected from the group consisting of an organic and inorganic anion such as nitrate, benzoate, phenylacetate, hydroxybenzoate, phenoxide, hydroxide, cyanide, nitrite; particularly preferred are chloride, bromide, iodide, methyl sulfate, ethyl sulfate and the like; M represents nitrogen, arsenic, or phosphorous. $R_1$, $R_2$, $R_3$ and $R_4$ are each independently selected from one of those groups consisting of hydrocarbyl and substituted hydrocarbyl provided that when one or both of $R_1$ and $R_2$ contain 1 to 4 carbon atoms, inclusive, the remainder of R moieties will each contain from 6 to 25 carbon atoms, or $R_1$ and $R_2$ may be taken together to represent a divalent moiety attached to the atom M, and which is selected from the group consisting of alkenylene and hydrocarbyl-substituted alkenylene having 5 to 10 carbon atoms, inclusive, in the ring thereof; or $R_1$ and $R_2$ may be taken together with the atom of M to which they are attached to represent a divalent or monovalent moiety selected from groups consisting of those having the formula:

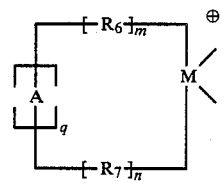

wherein A represents nitrogen, oxygen, sulfur, phosphorus and the like; and $R_6$ and $R_7$ are each selected from alkenylene and hydrocarbyl-substituted alkenylene of 1 to 25 carbon atoms, inclusive, m, n and q are each integers of 0 to 1 and the sum of m+n is 1 or 2. In all of these cases the groups are selected so that the total carbon atom content of the salt is at least twenty.

The term "halide" as used herein means the monovalent moiety obtained upon removal of a hydrogen atom from a parent hydrocarbon. Representative of hydrocarbyl are alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aryl of 6 to 25 carbon atoms, inclusive, such as phenyl, tolyl, xylyl, naphthyl, biphenyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undecenyl, dodecenyl, tridecenyl, pentadecenyl, octadecenyl, pentacosynyl and isomeric forms thereof.

The term "alkenylene" means the divalent moiety obtained on removal of two hydrogen atoms, each from a non-adjacent carbon atom of a parent hydrocarbon and includes alkenylene of 3 to 10 carbon atoms, inclusive, such as 1,3-propenylene, 1,4-butenylene, 1,5-pentenylene, 1,8-octenylene, 1,10-decenylene and the like.

The terms "substituted hydrocarbyl" and "substituted alkenylene" as used herein mean the hydrocarbyl or alkenylene moiety as previously defined wherein one or more hydrogen atoms have been replaced with an inert group, i.e. a chemical group which does not adversely affect the desired function of the organic quaternary salt of formula (I). Representative of such groups are aminophosphino-, hydrocarbyl, quaternary nitrogen (ammonium), quaternary phosphorous (phosphonium), hydroxyl-, alkoxy, mercapto-, alkyl, halo-, phosphate, phosphite, carboxylate groups and the like.

DETAILED DESCRIPTION OF THE PREFERRED EMBODIMENT OF THE INVENTION

The method of the invention may be employed to isomerize linalyl chloride to the geranyl and neryl chlorides according to the schematic formulae:

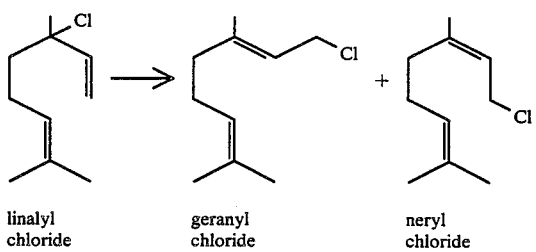

linalyl chloride     geranyl chloride     neryl chloride

The method of the invention is in improvement over isomerizations carried out in the presence of hydrogen halides and copper catalysts alone. Representative of hydrogen halides so employed are hydrogen chloride and hydrogen bromide. In general, catalytic proportions of the hydrogen halide are used and are essential to the invention as shown in the Examples (compare Ex. 3 and 12). Catalytic proportions are generally within the range of from about 0.01 to 5 percent by weight of the starting linalyl halides, preferably 0.1 to 1.0 percent.

The copper catalysts employed may be any copper compound having a valency of 2 or less, including metallic copper. Any copper compound convertible to the halide such as the bromide, iodide or chloride under conditions of the reaction may also be used. Representative of copper catalysts advantageously employed are the chloride, bromide, carbonate, oxide, acetate, formate, sulfate and like derivative cupric and cuprous compounds. Preferred as the copper catalyst in the improved process of the invention is cuprous chloride. Catalytic proportions of the copper catalyst are generally within the weight range of from about 0.01 to 2 percent of the allylic halide starting compound, preferably about 0.5 percent.

Organic quaternary compounds of the formula (I) given above are generally well known as are methods of their preparation. Representative of such organic quaternary compounds are trioctylmethylammonium chloride, tetraoctadecylammonium chloride, dodecyldimethylbenzylammonium chloride, tetradecyldimethylbenzylammonium chloride, hexadecyldimethylbenzylammonium chloride, N,N-cetylethylmorpholinium ethosulfate, methyl(1)cocoamidoethyl(2)cocoimidazolinium methyl sulfate, N-tallow-pentamethylpropanediammonium dichloride, trioctylmethylphosphonium bromide, N,N-soya ethylmorpholinium ethosulfate, hexadecylpyridinium chloride, benzyl hydroxyethyl(2)-cocoimidazolinium chloride, dodecyldimethil(ethylbenzyl)ammonium chloride, tetradecyldimethyl(ethylbenzyl)ammonium chloride, hexadecyldimethyl(ethylbenzyl)ammonium chloride, octadecyl-dimethyl(ethylbenzyl)ammonium chloride, octadecyldimethylbenzylammonium chloride, methyl bis (2-hydroxyethyl)cocoammonium chloride, methyl(1)soyaamidoethyl(2-)soyaimidazolinium methyl sulfate and the like.

Commercially available quaternary salts or purified forms of quaternary salts may be used in the preferred process of the invention. In any case, the carbon atom content of the quaternary salt must be at least twenty for the invention, as demonstrated in Examples 10 and 11.

It will be appreciated that under specific conditions of operating the process of the invention, certain of the above described compounds of the formula (I) given above have advantages over other compounds of the same general formula. Selection of a particular compound (I) for use under specific process conditions for optimum yields may be made by trial and error technique. We have observed however that there are advantages associated with a mixture of trialkylmethylammonium chlorides where the alkyl portion consists of a chain of from eight to ten carbon atoms. For example, Adogen 464 (Sherex Chemical Co.).

The organic quaternary salt is used in a proportion to isomerize at least some of the allylic halide according to the method of the invention. Such a proportion is generally within the range of from about 0.01 to 10 percent by weight of the halide charge, preferably 0.2 to 2.5 percent. Optimum proportions will depend to some extent upon the salt selected and may be determined by trial and error technique. Generally the preferred molar ratio of compound (I) to copper catalyst is from 0.01 to 5.0.

The method of the invention may be carried out by admixing the starting allylic halide with the hydrogen halide, copper catalyst and salt compound of the formula (I) in a suitable reaction vessel for a sufficient period of time to effect the desired isomerization. The controlling reaction rate in the method of the invention is the isomerization of the allylic halide to the desired allylic isomer. This is controlled by residence time in the reaction zone. We have found that in isomerization of linalyl chloride the preferred minimum total residence time is within the range of from 0.1 to 10 hours and most preferably 0.5 to 5 hours under preferred operating temperatures.

Although the method of the invention may be carried out under a range of operating temperatures, i.e, within the range of from about $-10°$ C. to $25°$ C., it is preferred to do so at a temperature of from $0°$ C. to $20°$ C., and most preferably, about $10°$ C.

The method of the invention is not dependent upon pressure, and may be carried out at atmospheric, subatmospheric or super-atmospheric pressures.

Progress of the isomerization may be monitored by conventional analytical techniques. When it has been determined that isomerization occurred to a maximum desired point, the product mixture may be passed from the reaction apparatus.

The following examples describe the manner the process of making and using the invention and set forth the best mode contemplated by the inventors of carrying out the invention but are not to be construed as limiting. All parts given are by weight unless otherwise indicated.

EXAMPLE 1

To 8.0 g of myrcene hydrochlorides, consisting of 37.0 parts linalyl chloride, 9.5 parts neryl chloride, 7.0 parts geranyl chloride, 5.0 parts alpha-terpinyl chloride and 41.5 parts hydrocarbons, was added 0.03 g cuprous chloride, 0.11g Adogen 464* and 0.2 g of hydrogen chloride gas. The mixture was stirred at $10°$ C. for 7 hours. Samples were withdrawn at 1-2 hour intervals, neutralized with aqueous sodium hydroxide, and analyzed by gas chromatography. Product content of linalyl, neryl and geranyl chloride (abbreviated LCl, NCl and GCl, respective) are shown below. The amount of time required to reduce the LCl content by one-half was 1 hour.

*A mixture of trialkylmethylammonium chlorides where the alkyl groups comprise 44% of $C_{10}$, 52% of $C_8$, 2% of $C_6$ and 2% of $C_{12}$.

| Time (Hrs) | Composition of Product (%) | | |
|---|---|---|---|
| | LCl | NCl | GCl |
| 0 | 37.0 | 9.5 | 7.0 |
| 1.5 | 10.5 | 16.4 | 23.5 |
| 3.0 | 7.2 | 17.2 | 25.5 |
| 6.5 | 5.1 | 17.5 | 26.8 |

EXAMPLES 2-12

Myrcene hydrochlorides were subjected to isomerization under the same conditions and amounts as described in Example 1 using 0.03 g cuprous chloride, 0.02 g hydrogen chloride gas, and an organic quaternary salt as described in Table 1 to obtain the results shown in Table 1 below. The Examples 10, 11 and 12 are not of the invention but are made for comparative purposes.

TABLE 1

| Example No. | Quaternary Salt And Amount Used | Amount of Time to Reduce LCl Content By One-half (hrs.) | GCl:NCl Ratio After 6.5 hours |
|---|---|---|---|
| 2 | None | 5-6 | 1.4 |
| 3 | Methyltrioctyl-ammonium chloride, 0.11 g | 1 | 1.4 |
| 4 | Dimethylbenzyl-stearyl ammonium chloride, 0.11 g | 1 | 1.6 |
| 5 | N,N—cetylethyl-morpholinium ethosulfate, 0.12 g | 1 | 1.7 |
| 6 | Benzyl hydroxy-ethyl(2)cocoimid-azolium chloride, 0.12 g | 1 | 1.8 |
| 7 | N—Tallowpenta-methyl propane diamonium dichloride, 0.12 g | 1 | 1.9 |
| 8 | Benzyltrioctyl-ammonium bromide, 0.14 g | 2 | 1.4 |
| 9 | Propyltriphenyl phosphonium bromide, 0.15 g | 3 | 1.4 |
| 10 | Trimethylbenzyl-ammonium chloride, 0.05 gm | >10 | 0.9 |
| 11 | Trimethylbutyl-ammonium bromide, 0.05 gm | >10 | 0.8 |
| 12 | Methytrioctyl-ammonium chloride, 0.11 g, with no HCl | >8 | 1.8 |

What is claimed:

1. A method for isomerizing linalyl halide to neryl and geranyl halides comprising isomerizing the linalyl halide in the presence of a catalytic proportion of a copper-containing catalyst, and further comprising carrying out the isomerization at a temperature below 25° C. in the presence of a catalytic proportion of an anyhydrous hydrogen halide and an organic quaternary ammonium or phosphonium salt which has a carbon atom content of at least twenty.

2. The process of claim 1 wherein the organic quaternary salt is selected from a group consisting of methyltrioctylammonium chloride, dimethylbenzylstearyl ammonium chloride, N,N-cetylethylmorpholinium ethosulfate, benzyl hydroxyethyl(2)-cocoimidazolium chloride, N-tallow pentamethyl propane diammoniumdichloride, benzyltrioctyl ammonium bromide and propyltriphenyl phosphonium bromide.

3. The process of claim 1 wherein the organic quaternary salt is a mixture of tri(alkyl)methyl ammonium chlorides where each alkyl portion comprises a chain of from eight to ten carbons.

4. The process of claim 1 preferably carried out at a temperature of about −10° C. to about 20° C.

5. The process of claim 1 wherein the copper catalyst is cuprous chloride.

6. The process of claim 5 wherein the catalytic proportion of copper catalyst is preferably within the weight range of about 0.01 to about 2.0% of linalyl halide.

7. The process of claim 1 wherein the molar ratio of organic quaternary salt to copper catalyst is preferably about 0.01 to about 5.0.

8. The process of claim 1 wherein the isomerization is preferably carried out for a period of about 0.1 to about 10.0 hours.

* * * * *